United States Patent
Grivas et al.

[11] Patent Number: 5,814,084
[45] Date of Patent: Sep. 29, 1998

[54] DIAPHYSIAL CORTICAL DOWEL

[75] Inventors: Nicholas E. Grivas, Charlotte, N.C.;
James M. Grooms, Gainesville, Fla.

[73] Assignee: University of Florida Tissue Bank, Inc., Alachua, Fla.

[21] Appl. No.: 587,070

[22] Filed: Jan. 16, 1996

[51] Int. Cl.⁶ ........................................ A61F 2/28
[52] U.S. Cl. .............................. 623/16; 623/17
[58] Field of Search .......................... 623/16, 17

[56] References Cited

U.S. PATENT DOCUMENTS

| | | |
|---|---|---|
| 3,848,601 | 11/1974 | Ma et al. . |
| 4,501,269 | 2/1985 | Bagby . |
| 4,714,469 | 12/1987 | Kenna . |
| 4,736,738 | 4/1988 | Lipovsek et al. . |
| 4,743,146 | 5/1988 | Khmelnitsky et al. . |
| 4,834,757 | 5/1989 | Brantigan ............................ 623/17 |
| 4,856,503 | 8/1989 | Schelhas . |
| 4,877,020 | 10/1989 | Vich . |
| 4,878,915 | 11/1989 | Brantigan . |
| 4,904,261 | 2/1990 | Dove et al. . |
| 4,936,848 | 6/1990 | Bagby ................................. 623/17 |
| 4,950,296 | 8/1990 | McIntyre ............................. 623/16 |
| 5,015,247 | 5/1991 | Michelson ............................ 606/61 |
| 5,015,255 | 5/1991 | Kuslich . |
| 5,026,373 | 6/1991 | Ray et al. . |
| 5,112,354 | 5/1992 | Sires .................................... 623/16 |
| 5,147,402 | 9/1992 | Bohler et al. . |
| 5,192,327 | 3/1993 | Brantigan . |
| 5,290,312 | 3/1994 | Kojimoto et al. . |
| 5,397,364 | 3/1995 | Kozak et al. . |
| 5,423,825 | 6/1995 | Levine . |
| 5,425,772 | 6/1995 | Brantigan . |
| 5,443,514 | 8/1995 | Steffee . |
| 5,458,638 | 10/1995 | Kuslich et al. . |
| 5,522,899 | 6/1996 | Michelson . |
| 5,593,409 | 1/1997 | Michelson ............................ 623/17 |
| 5,609,635 | 3/1997 | Michelson . |
| 5,645,598 | 7/1997 | Brosnahan, III . |

FOREIGN PATENT DOCUMENTS

| | | |
|---|---|---|
| 0 077 159 | 4/1983 | European Pat. Off. . |
| 0 307 241 | 3/1989 | European Pat. Off. . |
| U9500308 | 2/1995 | Spain . |
| WO 95/19797 | 7/1995 | WIPO . |

OTHER PUBLICATIONS

Vich, Jose M. Otero (1985) "Anterior cervical interbody fusion with threaded cylindrical bone" J. Neurosurg 63:750–753.

Catalog pages from the Musculoskeletal Transplant Foundation regarding The MTF EndoDowel™—General Information and Description/Ordering Information, two pages, date of publication unknown (believed to be Apr./May 1996).

Albee, F.H. et al. (1940) "The General Principles of Bone Grafting" Bone Graft Surgery in Disease, Injury and Deformity, Appleton–Century Company, Inc. (publisher), pp. xi–xv; 1–31; 48–107; and 210–227.

Musculoskeletal Transplant Foundation, Product catalog, Apr. 1996, 16 pages.

Musculoskeletal Transplant Foundation, "EndoDowel" product brochure, Oct. 1996, 3 pages.

Sofamor Danek, Laparoscopic bone dowel surgical technique, 1995, 15 pages.

Sofamor Danek, Laparoscopic bone dowel instrument catalog, Jun. 17, 1905, 1 page.

Unilab, Unilab "Surgibone" product profile, Date Unknown, 1 page.

Vich, Jose M. Otero, Update on the Cloward procedure: New instruments, Nov. 1, 1994, J. Neurosurg 81:716–720.

*Primary Examiner*—Randy C. Shay
*Attorney, Agent, or Firm*—Gerard H. Bencen, P.A.; Gerard H. Bencen, Esq.

[57] ABSTRACT

A dowel is provided by obtaining a plug from the shaft (diaphysis) of various long bones. The dowel has an intramedullary canal which can be packed with any of a variety of osteogenic materials. The dowel has a cortical surface into which an instrument attachment hole may be machined and onto which an alignment mark may be inscribed for proper orientation of the intra-medullary canal. The dowel has a chamfered insertion end and has improved biomechanical and vertebral fusion induction properties as compared to standard dowels known in the art.

26 Claims, 4 Drawing Sheets

DIAPHYSIAL CORTICAL DOWEL

BACKGROUND OF THE INVENTION i. Field of the Invention

The invention provides a novel dowel machined from the cortex of bone diaphyses and methods of use thereof.

ii. Background

It is common for patients presenting with spinal trauma or pathology to require the fusion of two or more vertebra. In the art, a standard solution to this problem is to create a cavity between two adjacent vertebra to accept the insertion of a dowel made from bone or another material. For this purpose, a dowel known as the Cloward Dowel has been in use for many years. That device is a generally circular pin made by drilling an allogeneic or autogenic plug from the cancellous bone of the ilium (i.e., the hip bone). As such, this bone has two cortical surfaces (i.e., it is bicortical) and has an open, latticed or porous structure between the two cortical surfaces. Unfortunately, such dowels have very poor biomechanical properties, principally being susceptible to compression. Accordingly, such dowels present the major danger of collapsing prior to fusion of the adjacent vertebra between which such a dowel is inserted.

A dowel of greater biomechanical properties has been produced from allogeneic femoral or tibial condyles (i.e., the rounded prominence at the end of the femur or tibia where such bones articulate with other bones). The result of drilling a plug from such a condyle is a unicortical dowel. Such unicortical dowels are available from most tissue banks, including the University of Florida Tissue Bank, Inc., (see, for example, our Allograft Catalog, product numbers 280012, 280014, and 280016; this catalog and these products are available on request by calling 904-462-3097, or by calling 1-800-OAGRAFT, or by writing to the University of Florida Tissue Bank, Inc., 1 Progress Boulevard., P.O. Box 31, S. Wing, Alachua, Fla. 32615). While such unicortical dowels represent a major advance over the bicortical dowels of Cloward, described above, from a biomechanical point of view, the biomechanical properties of the diaphysial cortical dowel of the instant invention is expected to represent a substantial improvement over the unicortical dowels, due to the greater density of source bone, as will be evident from a reading of the full disclosure which follows.

In addition to the known Cloward and unicortical dowels, a number of United States patents have been found dealing with the general area of dowels for achieving vertebral fusions. Thus, for example, U.S. Pat. No. 5,015,247 discloses a threaded spinal implant which, when placed between two adjacent vertebrae, directly participates and is incorporated in the ensuing fusion. The implant is made of a hollow metal casing which is filled with osteogenic material. A plurality of perforations are provided in the casing so that bone can grow into and out of the implant. Metal threads and tabs are provided to insert and prevent backing out of the implant, respectively. However, that implant is made out of metal and thus is a foreign object which is inserted into the spine and is thus never fully incorporated into the fusion. Furthermore, as the implant is preferably made of titanium, production of the implant requires the use of specialized metal molding and machining, and production of the implant material itself, which is expensive. A further major disadvantage of such a device is that it requires FDA approval for use, while the FDA has already approved grafting of human bones. Accordingly, the implant disclosed in the U.S. Pat. No. '247 is quite different from the diaphysial cortical dowel of the instant invention. Likewise for the many patents reviewed in the background section of that patent, to which the reader's attention is directed for a further understanding of the background of the instant invention. The disclosure of the U.S. Pat. No. '247 is hereby incorporated by reference for this purpose.

In U.S. Pat. No. 4,627,853, a method of producing a prosthesis for replacement of articular cartilage and the prostheses so produced is disclosed. The prostheses of the U.S. Pat. No. '853, principally designed for articulating cartilage replacement, are machined from allogenic or xenogeneic bone segments and then demineralized to produce a bone fragment with a spongy texture similar to natural cartilage. The prostheses are also tanned to render the material non-antigenic. While the methods of the U.S. Pat. No. '853 may be used to alter the properties of the diaphysial cortical dowel of the instant invention, and the disclosure of the U.S. Pat. No. '853 is herein incorporated by reference for that purpose, the U.S. Pat. No. '853 does not teach or suggest the novel device and method of the instant invention. While it is alleged that discs in the spinal column are among the uses for the prostheses of the U.S. Pat. No. '853, and while there is some discussion of the ability to machine bone, there is no disclosure of the use of diaphysial cortical segments to make dowels, nor is there any disclosure of the particular advantages achievable by use of such bone segments, as is disclosed herein.

In U.S. Pat. No. 5,053,049, a flexible prosthesis and a method for making such prostheses are disclosed. The process includes machining a bone, demineralizing the bone to impart a desired degree of flexibility, and tanning to render the material non-antigenic. This patent is generally similar in disclosure to the disclosure found in the U.S. Pat. No. '853 discussed above, except that the particular applicability of the disclosed process to the production of an outer ear prosthesis is emphasized. A particular claim is directed to the production of a spinal disc. However, there is no disclosure of the use of diaphysial cortical segments to make dowels, nor is there any disclosure of the particular advantages achievable by use of such bone segments, as is disclosed herein.

In U.S. Pat. No. 5,306,303, a bone induction method is disclosed which consists of implanting a bone morphogenetic, protein-free ceramic in the soft tissue or bone of an animal. The ceramic disclosed as preferable is calcium phosphate and the use of such material for achieving spinal intervertebral joint fusions (disk arthroplasty) is suggested. The material and product of the U.S. Pat. No. '303, aside from its possible use for a purpose similar to that for which the instant product is designed, bears little or no resemblance to the instant invention.

In U.S. Pat. No. 5,171,279, a method for subcutaneous suprafascial pedicular internal fixation of vertebrae of the spine is disclosed to facilitate graft fusion. The method included excision of the nucleus of an affected disc, preparation of a bone graft, instrumentation of the vertebrae for fixation, and introduction of a bone graft into the resected nuclear space. Metallic fixation hardware is disclosed as the principal aspect of the claimed invention. Accordingly, aside from dealing with the same general problem, the invention disclosed and claimed in the U.S. Pat. No. '279 bears little resemblance to the diaphysial cortical dowel and method of the instant invention.

Accordingly, having reviewed the solutions attempted in the field prior to the instant disclosure, it is concluded that there remains the need for a vertebral fusion implant which has superior biomechanical and vertebral fusion promoting properties. The instant invention provides such an implant as well as a method for making and using the implant.

BRIEF SUMMARY OF THE INVENTION

The diaphysial cortical dowel of this invention is an implant useful in cervical or thoracic and lumbar fusions. For cervical fusions, the dowel is preferably obtained from the allogeneic fibula, radius, ulna and occasionally, from small humeri. The dimensions of such dowels are typically between about 8–15 mm in length (depth) and about 10–14 mm in diameter. For thoracic and lumbar fusions, the dowel is preferably obtained from the humerus, femur or tibia. The dimensions of such dowels are typically between about 10–30 mm in length (depth) and about 14–20 mm in diameter. In each case, the dowel is obtained as a transverse plug from the diaphysis of these bones. Accordingly, each dowel has the feature of having the natural intramedullary canal of the source bone forming a cavity through the dowel, perpendicular to the length of the dowel, which can be pre-packed with allogeneic cancellous bone, autogenous bone fragments, hydroxyapatite, bioglass, mixtures of these elements or any other bioceramic or osteogenic material to promote rapid fusion of the vertebrae between which the dowel is inserted.

The method for preparing and using the diaphysial cortical dowel of this invention comprises the steps of obtaining a plug from the diaphysis of an appropriate donor bone. Typically, the donor will have been extensively screened for communicable diseases, cancer, and at-risk behavior prior to acceptance of the donor bone for dowel formation. The plug is then machined, preferably in a class 10 clean room, to the dimensions desired. Optionally, a groove is inscribed on the circumference of the dowel to prevent backing-out of the dowel. Another option is to inscribe a thread onto the circumference of the dowel. Chamfering of the forward end of the dowel which is to be inserted into a cavity formed between adjacent vertebrae is also preferred. The curvature of the chamfered end aids in the ease of insertion. Preferably, an instrument attachment hole is machined in the opposite end of the dowel from the chamfered end. Preferably, a score mark is inscribed on the cortical end into which the instrument attachment hole is machined so that the surgeon can align the intra-medullary canal so that the canal is parallel with the length of the recipient's spinal column.

In use, the surgeon creates a cavity between two adjacent vertebra that are to be fused. The autogenous bone fragments may be collected and packed into the intra-medullary canal of the diaphysial cortical dowel, or the dowel may be used with a pre-packed osteogenic composition. The dowel is mounted on an instrument via the instrument attachment hole and carefully inserted into the cavity created between the adjacent vertebrae to be fused. Over a period of several months, it is found that substantial fusion of the adjacent vertebrae occurs.

Accordingly, it is one object of this invention to provide a diaphysial cortical dowel made from bone for insertion between vertebrae to be fused.

Another object is to improve patient incidence of safe and satisfactory fusion.

Another object of this invention is to provide a dowel for vertebral fusions which has improved biomechanical properties over standard Cloward Dowels and unicortical dowels known in the art.

Another object of this invention is to provide a dowel with improved osteogenic and vertebral fusion promoting capacity.

Another object of this invention is to provide a dowel with a natural canal running therethrough to accept packing having osteogenic properties.

Another object of this invention is to provide a method for making a novel diaphysial cortical dowel.

Another object of this invention is to provide a method for using the novel diaphysial cortical dowel of this invention.

Additional objects and advantages of the diaphysial cortical dowel of this invention will become apparent from the full disclosure which follows.

DETAILED DESCRIPTION OF THE INVENTION

Figure 1A:
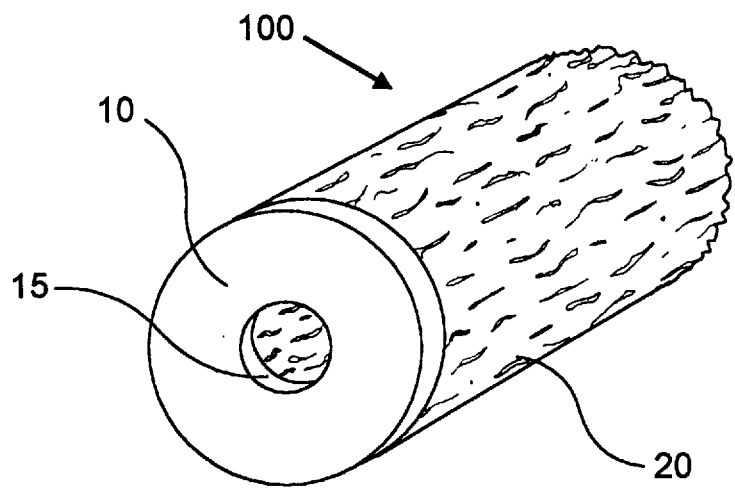
FIG. 1A depicts the structure of a standard unicortical dowel known in the art.

The diaphysial cortical dowel of this invention is an implant useful in cervical or thoracic and lumbar fusions. For cervical fusions, the dowel is preferably obtained from the fibula, radius, ulna and occasionally, from small humeri. The dimensions of such dowels are typically between about 8–15 mm in length (depth) and about 10–14 mm in diameter. For thoracic and lumbar fusions, the dowel is preferably obtained from the humerus, femur or tibia. The dimensions of such dowels are typically between about 10–30 mm in length (depth) and about 14–20 mm in diameter. In each case, the dowel is obtained as a transverse plug from the diaphysis of these long bones. Preferably, the bone plugs are obtained using a diamond tipped cutting bit which is water cleaned and cooled. Commercially available bits having a generally circular nature and an internal vacant diameter between about 10 mm to about 20 mm are amenable to use for obtention of these bone plugs. Such core drills are available, for example, from Starlite, Inc. A machine for obtention of endo- and cortical dowels consists of a pneumatic driven miniature lathe which is fabricated from stainless steel and anodized aluminum. It has a spring loaded carriage which travels parallel to the cutter. The carriage rides on two runners which are 1.0 inch stainless rods and has a travel distance of approximately 8.0 inches. One runner has set pin holes on the running rod which will stop the carriage from moving when the set pin is placed into the desired hole. The carriage is moveable from side to side with a knob which has graduations in metric and in English. This allows the graft to be positioned. On this carriage is a vice which clamps the graft and holds it in place while the dowel is being cut. The vice has a cut out area in the jaws to allow clearance for the cutter. The lathe has a drive system which is a pneumatic motor with a valve controller which allows a desired RPM to be set.

First, the carriage is manually pulled back and locked in place with a set pin. Second, the graft is loaded into the vice and is aligned with the cutter. Third, the machine is started and the RPM is set, by using a knob on the valve control. Fourth, the set pin, which allows the graft to be loaded onto the cutter to cut the dowel. Once the cutter has cut all the way through the graft, the carriage will stop on a set pin. Fifth, sterile water is used to eject dowel out of the cutter. It is fully autoclavable and has a stainless steel vice and/or clamping fixture to hold grafts for cutting dowels. The graft can be positioned to within 0.001" of an inch which creates dowel uniformity during the cutting process.

The cutter used in conjunction with the above machine can produce dowels ranging from 5 mm to 30 mm diameters and the sizes of the cutters are 10.6 mm; 11.0 mm; 12.0 mm; 13.0 mm; 14.0 mm; 16.0 mm; and 18.0 mm. The composition of the cutters is stainless steel with a diamond powder cutting surface which produces a very smooth surface on the wall of the dowels. In addition, sterile water is used to cool and remove debris from graft and/or dowel as the dowel is being cut (hydro infusion). The water travels down through the center of the cutter to irrigate as well as clean the dowel under pressure. In addition, the water aides in ejecting the dowel from the cutter.

Plugs having a depth of about 8 mm to about 30 mm are generally acceptable, with appropriate gradations in length and diameter naturally being available at the option of the machinist. Accordingly, for cervical dowels, also referred to herein as anterior cervical fusion or ACF dowels, lengths of 8 mm, 9 mm, up to about 15 mm are desirable. Dowels of differing diameter are most conveniently obtained as follows:

| Diameter | Source |
| --- | --- |
| 10.6–11 mm | fibula |
| 12 mm | radius |
| 14 mm | ulna |
| 14+ mm | small humeri |

Dowels for thoracic and lumbar fusions, also referred to herein as anterior thoracic inner body fusion (ATIF) and anterior lumbar inner body fusion (ALIF) dowels, respectively, having a depth of between about 10–30 mm, and preferably between about 15–24 mm, are generally acceptable, depending on the needs of a particular patient. Dowels of differing diameter for thoracic and lumbar fusions are most conveniently obtained as follows:

| Diameter | Source |
| --- | --- |
| 14–16 mm | humerus |
| 16–18 mm | femur |
| 18–20 mm | tibia |

In every case, a consenting donor (i.e., a donor card or other form of acceptance to serve as a donor) is screened for a wide variety of communicable diseases and pathogens, including human immunodeficiency virus, cytomegalovirus, hepatitis B, hepatitis C and several other pathogens. These tests may be conducted by any of a number of means conventional in the art, including but not limited to ELISA assays, PCR assays, or hemagglutination. Such testing follows the requirements of: (i) American Association of Tissue Banks, Technical Manual for Tissue Banking, Technical Manual—Musculoskeletal Tissues, pages M19–M20; (ii) The Food and Drug Administration, Interim Rule, Federal Register/Vol. 58, No. 238/Tuesday, Dec. 14, 1993/Rules and Regulations/65517, D. Infectious Disease Testing and Donor Screening; (iii) MMWR/Vol. 43/No. RR-8, Guidelines for Preventing Transmission of Human Immunodeficiency Virus Through Transplantation of Human Tissue and Organs, pages 4–7; (iv) Florida Administrative Weekly, Vol. 10, No. 34, Aug. 21, 1992, 59A-1.001-014 59A-1.005(12) (c), F.A.C., (12) (a)–(h), 59A-1.005(15), F.A.C., (4) (a)–(8). In addition to a battery of standard biochemical assays, the donor, or their next of kin, is interviewed to ascertain whether the donor engaged in any of a number of high risk behaviors such as having multiple sexual partners, suffering from hemophilia, engaging in intravenous drug use etc. Once a donor has been ascertained to be acceptable, the bones useful for obtention of the dowels as described above are recovered and cleaned. The final machined product may be stored, frozen or freeze-dried and vacuum sealed for later use.

Since the dowels are obtained from transverse plugs across the diaphysis of long bones, each dowel has the feature of having the natural intra-medullary canal of the source bone forming a cavity through the dowel perpendicular to the length of the dowel. The canal cavity in the long bone is, in vivo, filled with bone-marrow. In the standard Cloward Dowel and unicortical dowels known in the art, no such natural cavity exists and the cancellous bone that forms the body of such dowels tends to be too brittle to accept machining of such a cavity. The instant dowels, by the nature of their origin, are already available with such a cavity. Naturally, based on this disclosure, those skilled in the art will recognize that other bone sources could be used which do not have the intra-medullary canal, and if sufficient strength is inherent to the bone, such a canal could be machined. Accordingly, such an extension of this invention should be considered as an obvious variant hereof and comes within the claims appended hereto. The marrow is removed from the intra-medullary canal of the diaphysial plugs and the cavity is cleaned. The cavity can then be packed with autogenous bone fragments from the recipient (i.e., when the cavity between adjacent vertebrae is formed, the removed bone fragments can be used as an autogenous packing), hydroxyapatite, BIOGLASS®, mixtures of these elements or any other osteogenic material to promote rapid fusion of the vertebrae between which the dowel is inserted. Bioactive glasses are generally composed of $SiO_2$, $Na_2O$, CaO, and $P_2O_5$. A preferred bioactive glass, BIOGLASS® 45S5 contains these compounds in the following respective weights: 45%, 24.5%, 24.4%, and 6%. As is evident from a review of *An Introduction to Bioceramics*, edited by Larry L. Hench and June Wilson (World Scientific Publishing Co. Pte. Ltd, 1993, volume 1), there is a vast array of bioceramic materials, including BIOGLASS®, hydroxyapatite and calcium phosphate compositions known in the art which can be used to advantage for this purpose. That disclosure is herein incorporated by reference for this purpose.

Figure 3A:
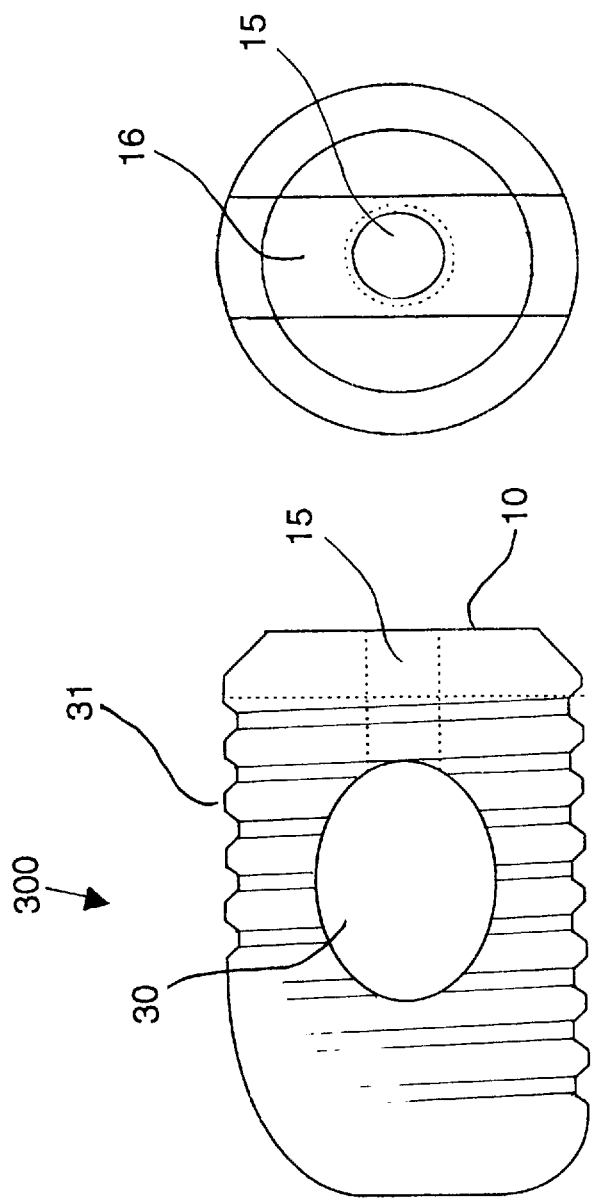
FIG. 3A depicts one embodiment of this invention in which the dowel is threaded.
Figure 3B:
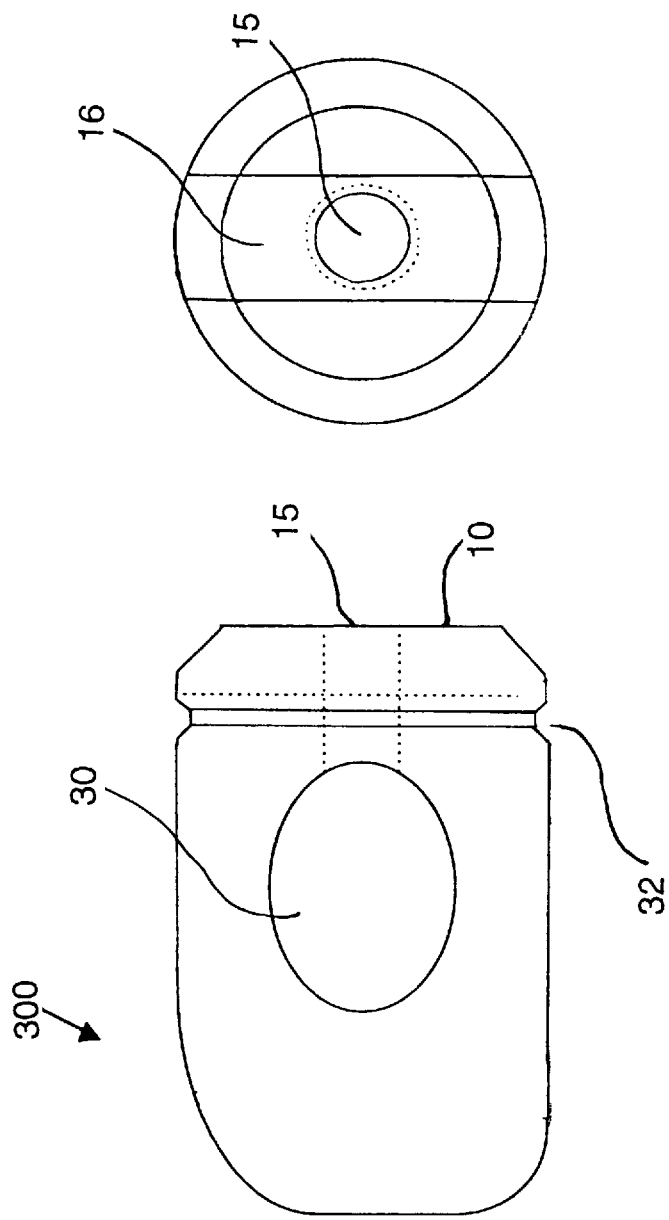
FIG. 3B depicts one embodiment of this invention in which the dowel is grooved.

The method for preparing and using the diaphysial cortical dowel of this invention comprises the steps of obtaining a plug from the diaphysis of an appropriate donor bone. As described above, the donor will have been extensively screened for communicable diseases, cancer, and at-risk behavior prior to acceptance of the donor bone for dowel formation. The plug is then machined, preferably in a class 10 clean room, to the dimensions desired. The machining is preferably conducted on a lathe such as a jeweler's lathe or machining tools may be specifically designed and adapted for this purpose. Specific tolerances for the dowels and reproduceability of the product dimensions are important features for the successful use of such dowels in the clinical setting. Optionally, a groove 32 (see FIG. 3B) is inscribed on the circumference of the dowel to prevent backing-out of the dowel, thereby forming a "rib" on the dowel which acts as a stop. Another option is to inscribe a thread 31 (see FIG. 3A) onto the circumference of the dowel. Machining of such grooves and threads on standard Cloward Dowels and even on unicortical dowels known in the art is difficult if not impossible due to the brittle cancellous nature of such dowels. Accordingly, the dowels of this invention have the advantage of having very good biomechanical properties amenable to such machining.

The forward end of the dowel which is to be inserted into a cavity formed between adjacent vertebrae is preferably chamfered by appropriate abrasive means known in the art such as machining, filing or sanding. The curvature of the chamfered end aids in the ease of insertion. The tolerance for the chamfering is fairly liberal and the desired object is merely to round or slightly point the end of the dowel that is to be inserted into the cavity formed between adjacent vertebrae to be fused.

Preferably, opposite the chamfered end, an instrument attachment hole is machined, for example by drilling. It is preferable that this end have a generally flat surface to accept the instrument for insertion of the dowel into the recipient. Preferably, the dowel will be of such dimensions as to fit standard insertion tools, such as those produced by Midas-Rex, Inc. In addition, it is preferred that a score mark be inscribed on the instrument attachment site of the dowel so that the surgeon can align the intra-medullary canal so that the canal is parallel with the length of the recipient's spinal column. With the aid of the score mark, once the dowel is inserted into the intervertebral cavity that is formed by the surgeon, even once the canal is no longer visible, proper alignment is possible.

Referring to FIG. 1, there is shown, in FIG. 1A the standard unicortical dowel 100 known in the art, having a cortical surface 10, a drilled instrument attachment hole 15, and a body of brittle cancellous bone 20.

Figure 1B:
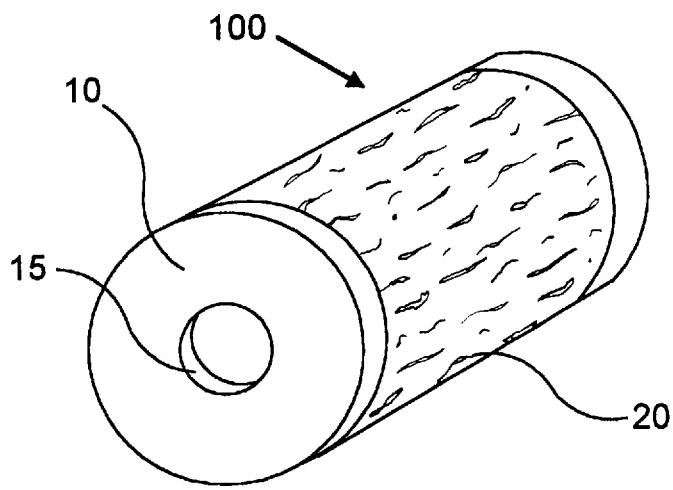
FIG. 1B depicts the structure of a standard Cloward Dowel known in the art.

In FIG. 1B, there is shown the standard bicortical dowel 200 known in the art having two cortical surfaces 10, a drilled instrument attachment hole 15, and a body of brittle cancellous bone 20.

Figure 1C:
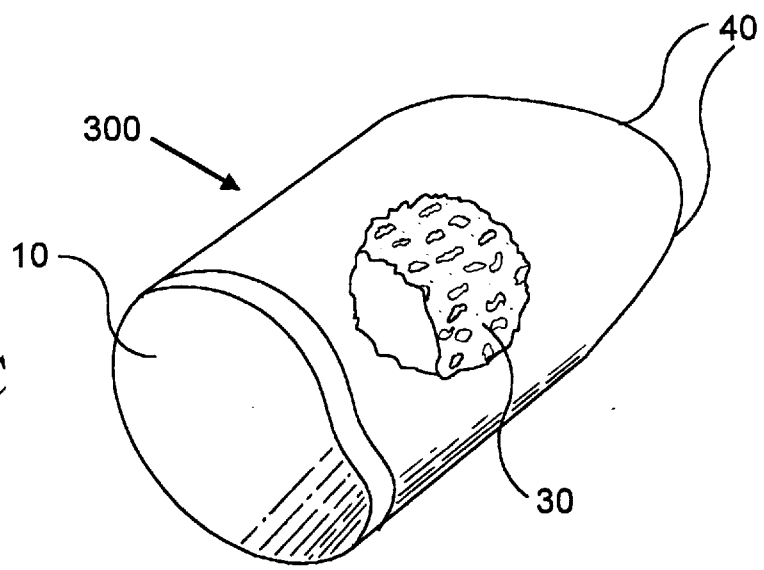
FIG. 1C depicts the structure of one embodiment of the diaphysial cortical dowel of this invention.

In FIG. 1C, the novel dowel 300 of this invention is shown having a cortical surface 10 into which an instrument attachment hole 15 and alignment score mark 16 may be machined (not shown as these elements are optional but preferred). Also shown is the intramedullary canal 30 and the chamfered insertion end 40 (also optional but preferred). Also not shown but easily inscribed due to the strength of the dowel 300 are circumferential ribbing or threads.

Figure 2B:
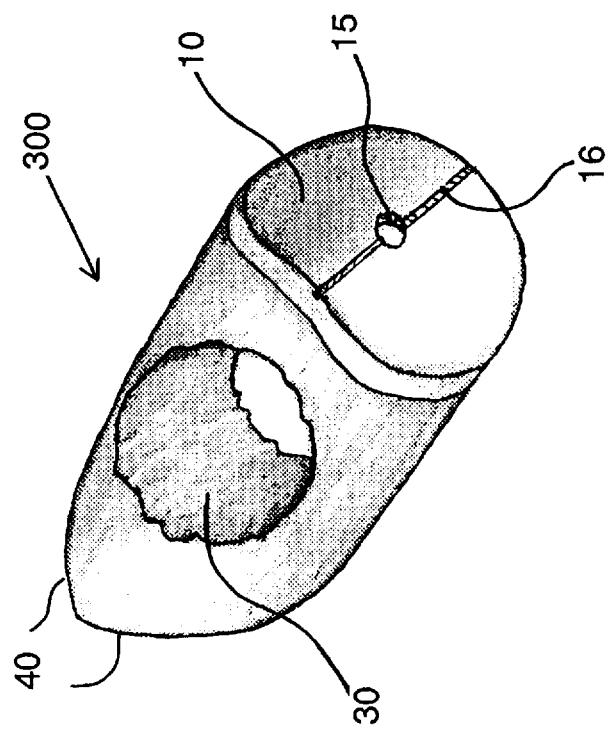
FIG. 2B depicts the ATIF or ALIF dowel with the instrument attachment hole and score mark.
Figure 2A:
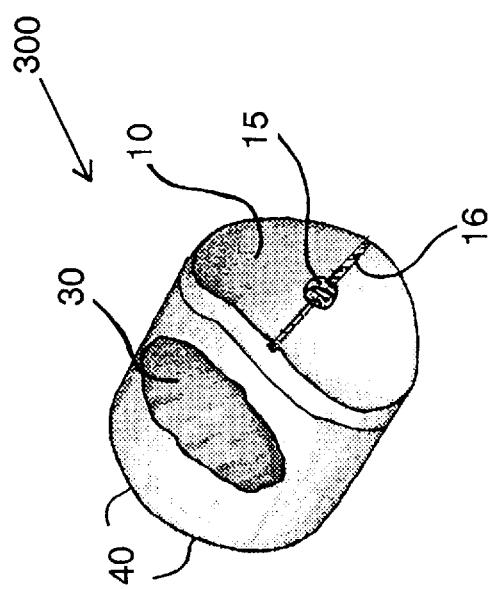
FIG. 2A depicts the ACF dowel with the instrument attachment hole and score mark.

Referring to FIG. 2, there is shown the ACF dowel in FIG. 2A and the ATIF or the ALIF dowel in FIG. 2B. Also shown, in addition to what is shown in FIG. 1, are the score mark 16 and the instrument hole 15.

In use, the surgeon creates a cavity between adjacent vertebrae that are to be fused. The autogenous bone fragments produced in the formation of the cavity may be collected and packed into the intra-medullary canal of the diaphysial cortical dowel, or the dowel may be used with a pre-packed osteogenic composition. A dowel of the appropriate dimensions is selected by the surgeon, based on the size of the cavity created and the needs of the particular patient undergoing the fusion. The dowel is mounted on an instrument via the instrument attachment hole and carefully inserted into the cavity created between the adjacent vertebra to be fused. For cervical fusions, only one dowel is needed. For lumbar fusions, two dowels may be required. In any event, the dowels may be applied laparoscopically using currently available instrumentation. Over a period of several months, it is found that substantial fusion of the adjacent vertebrae occurs.

While the foregoing description describes this invention, including its best mode, those skilled in the art will recognize that any of a number of variations on the basic theme disclosed herein can be made. Thus, for example, differing shapes can be made from the diaphysis of various bones and could be used for other orthopaedic purposes than vertebral fusions. In addition, any of a number of know bone treatments can be applied to the dowel of this invention to alter its properties. For example, the methods disclosed in U.S. Pat. Nos. 4,627,853; 5,053,049; 5,306,303; and 5,171,279 can be adapted and applied to the invention disclosed herein. Accordingly, the disclosures of those patents is herein incorporated by reference for this purpose.

EXAMPLE 1

Biomechanical Testing of ACF Dowels

Purpose: To describe the results from the compression testing of ACF dowels.

Materials: Instron Machine, ACF Dowels, Graph Recording Paper, Pen.

Procedure: The procedure utilized the above materials to compress the ACF dowels to failure and calculate their rupture modulus.

Preparing the dowel for compression:

Wipe the residual moisture from the surface of the dowel.

Set Instron for desired full scale load, crosshead speed, and paper speed.

Position dowel under compression head with hole up.

Testing procedures:

Start the graph paper to record the composition load.

Start the Instron to compress the dowel.

Stop and release the load when failure is achieved or the machine is at a maximum compression load and the dowel does not fail.

Results: The dowels were all compressed to failure. The results from the testing is included in the data below.

| Maximum Load | Minimum Load | Mean Load | Median |
| --- | --- | --- | --- |
| 383 kg | 200 kg | 267.14 kg | 264 kg |
| 3743 Newtons | 1960 Newtons | 2618 Newtons | 2587 Newtons |

EXAMPLE 2

Biomechanical Testing of ATIF & ALIF Dowels

Purpose: To describe the results from the compression testing of the ATIF & ALIF dowels.

Materials: Instron Machine, ATIF & ALIF Dowels, Graph Recording Paper, Pen.

Procedure: The procedure utilized the above materials to compress the dowels to failure and calculate their rupture modulus.

Preparing the dowel for compression:

Wipe the residual moisture from the surface of the dowel.

Set Instron for desired full scale load, crosshead speed, and paper speed.

Position dowel under compression head with the hole up.

Testing procedures:

Start the graph paper to record the compression load.

Start the Instron to compress the dowel.

Stop and release the load when failure is achieved or the machine is at a maximum compression load and the dowel does not fail.

Results: The ATIF & ALIF dowels were tested in the above manner and did not fail with a compression load of 500 kg (4900 Newtons). This is the Instron's maximum load.

EXAMPLE 3

Cervical Fusion Using Diaphysial Cortical Dowel

Preoperative Diagnosis. Ruptured cervical disc and spondylosis C5-6.

Postoperative Diagnosis. Same.

Operative Procedure. Anterior cervical discectomy and fusion C5-6.

After satisfactory general endotracheal anesthesia in the supine position, the patient was prepped and draped in the routine fashion. Incision was made in the skin length of the neck and carried through the platysma muscle. Dissection was carried down to expose the anterior vertebral column and the appropriate space identified by x-ray. Discectomy and foraminotomy were then performed and there was found a central, extruded fragment of disc toward the right side. When adequate decompression had been achieved, a bone dowel was cut from bone bank fibula and counter-sunk between the vertebral bodies to afford distraction. The wound was then irrigated with Bacitracin and closed in layers with Dexon and steri strips.

Postoperative evaluation and subsequent patient monitoring revealed successful operative outcome and good vertebral fusion.

It should be understood that the examples and embodiments described herein are for illustrative purposes only and that various modifications or changes in light thereof will be suggested to persons skilled in the art and are to be included within the spirit and purview of this application and the scope of the appended claims.

REFERENCES

U.S. Pat. No. 5,015,247
U.S. Pat. No. 4,627,853
U.S. Pat. No. 5,053,049
U.S. Pat. No. 5,306,303
U.S. Pat. No. 5,171,279
University of Florida Tissue Bank, Inc. Allograft Catalog.
An Introduction of Bioceramics (1993), Hench, Larry L., June Wilson (eds.), World Scientific Publishing Co. Pte. Ltd., volume 1.

We claim:

1. A diaphysial cortical bone dowel comprising a transverse bone plug obtained from a transverse cut in the diaphysis of a long bone having an intra-medullary canal, said plug having a canal running therethrough, wherein said canal is defined by the intra-medullary canal of said long bone and wherein said plug retains the natural architecture surrounding said intra-medullary canal.

2. The diaphysial cortical dowel of claim 1 having a chamfered end.

3. The diaphysial cortical dowel of claim 2 wherein the end opposite the chamfered end has an instrument attachment hole machined therein.

4. The diaphysial cortical dowel of claim 3 wherein the end having the instrument attachment hole also has a score mark inscribed therein.

5. The diaphysial dowel of claim 1 further comprising an external feature machined into the circumference of the dowel.

6. The diaphysial cortical dowel of claim 5 wherein said feature includes a groove.

7. The diaphysial cortical dowel of claim 5 wherein said feature includes threads formed along a portion of the length of the dowel.

8. The diaphysial cortical dowel of claim 1 having a length of between 8 mm and about 30 mm.

9. The diaphysial cortical dowel of claim 8 having a diameter of between about 10 mm and about 24 mm.

10. The diaphysial cortical dowel of claim 1 further comprising an osteogenic composition packed within said canal.

11. The diaphysial cortical dowel of claim 10 wherein said osteogenic composition is autogenous bone, hydroxyapatite, bioglass, a calcium phosphate ceramic or a mixture of these.

12. The diaphysial cortical dowel of claim 1 obtained as a transverse plug from the shaft of a donor's fibula, radius, ulna, humerus, femur or tibia.

13. The diaphysial cortical dowel of claim 1 prepared by a process which comprises machining a transverse plug from a transverse cut in the diaphysis of a donor's fibula, radius, ulna, humerus, femur or tibia, said plug having a diameter of between about 10 mm and about 24 mm and a length of between about 8 mm and about 30 mm such that the resulting plug retains the natural architecture surrounding the canal running therethrough, wherein said canal is defined by the intra-medullary canal of said long bone.

14. The diaphysial cortical dowel of claim 13 wherein said process of preparation further comprises chamfering one end of said plug to form a generally curved surface for ease of insertion of the dowel into an intervertebral cavity.

15. The diaphysial cortical dowel of claim 14 wherein said process of preparation further comprises machining an instrument attachment hole into the end of the dowel opposite the chamfered end and inscribing a score mark on the instrument attachment end of the dowel to allow for proper alignment of the intra-medullary canal.

16. A method of making a dowel which comprises machining a transverse plug as a transverse cut across the diaphysis of a donor's fibula, radius, ulna, humerus, femur or tibia, said plug having a diameter of between about 10 mm and about 24 mm and a length of between about 8 mm and about 30 mm such that the resulting plug has, running through it, perpendicular to the long axis of the plug, a canal defined by a portion of the natural intra-medullary canal of the donor's bone.

17. The method of claim 16 further comprising chamfering one end of said plug to form a generally curved surface for ease of insertion of the dowel into an intervertebral cavity.

18. The method of claim 16 further comprising machining an instrument attachment hole into the end of the dowel opposite the chamfered end.

19. The method of claim 18 further comprising inscribing a score mark on the instrument attachment end of the dowel to allow for proper alignment of the intra-medullary canal.

20. A method for fusing vertebrae which comprises making a cavity between the vertebrae to be fused and inserting therein a diaphysial cortical dowel comprising a transverse bone plug obtained from a transverse cut in the diaphysis of a long bone having an intra-medullary canal, wherein said canal is defined by the intra-medullary canal of said long bone, and wherein said plug retains the natural architecture surrounding the intra-medullary canal running therethrough.

21. The method of claim 20 further comprising retention of bone fragments obtained during the making of said cavity between said vertebrae to be fused and packing said bone fragments into the intramedullary canal of said diaphysial cortical dowel.

22. The method of claim 21 wherein said osteogenic composition is autogenous bone fragments obtained during the making of said cavity between said vertebrae to be fused, a bioceramic, bioglass, hydroxyapatite, calcium phosphate or a combination of these.

23. The method of claim 20 further comprising packing the intra-medullary canal of the diaphysial cortical dowel with an osteogenic composition.

24. An implant for insertion into at least one bore formed between opposing vertebrae of a spine where the vertebrae are separated by a space and each vertebra has end plates, the implant comprising:

(a) a solid generally cylindrical body having a first and a second end, and an outer surface, opposing sides and a longitudinal axis;

(b) the body having threads on a portion of the outer surface between the first and second end, the threads configured for threading into bone;

(c) the body including at least one through canal perpendicular to the longitudinal axis positioned between opposing sides, the through canal containing a biocompatible porous material for allowing the growth of bone through the canal; and (d) the through canal being positioned between generally opposing sides of the body so as to provide contact between the biocompatible porous material and the end plates of the opposing vertebrae when the implant is inserted into at least one bore formed between opposing vertebrae;

provided that said implant is composed substantially of cortical bone, that said implant comprises a transverse plug obtained from a transverse cut across the diaphysis of a long bone, and that said canal is defined by the intra-medullary canal of a long bone, and wherein said body retains the natural architecture surrounding said intra-medullary canal.

25. A method for making an implant for insertion into a space formed between adjacent vertebrae comprising obtaining a plug of substantially cortical bone by cutting transversely across the diaphysis of a long bone such that a bone plug having a longitudinal axis is thereby produced having a canal running through the bone plug perpendicular to the longitudinal axis of the plug, wherein said canal is defined by the natural intra-medullary canal of said long bone, and wherein said plug retains the natural architecture surrounding the intra-medullary canal.

26. A diaphysial cortical bone dowel comprising a transverse bone plug obtained from a transverse cut in the diaphysis of a long bone having an intra-medullary canal, said plug comprising a canal running therethrough, wherein said canal is defined by a portion of the natural intra-medullary canal of said long bone.

* * * * *